US008710280B2

(12) United States Patent
Warner et al.

(10) Patent No.: US 8,710,280 B2
(45) Date of Patent: Apr. 29, 2014

(54) WEAK ACID RECOVERY SYSTEM FOR ETHANOL SEPARATION PROCESSES

(75) Inventors: R. Jay Warner, Houston, TX (US); Trinity Horton, Houston, TX (US); Radmila Jevtic, Pasadena, TX (US); Victor J. Johnston, Houston, TX (US); David Lee, Seabrook, TX (US); Adam Orosco, Houston, TX (US); Lincoln Sarager, Houston, TX (US)

(73) Assignee: Celanese International Corporation, Dallas, TX (US)

( * ) Notice: Subject to any disclaimer, the term of this patent is extended or adjusted under 35 U.S.C. 154(b) by 298 days.

(21) Appl. No.: 13/094,722

(22) Filed: Apr. 26, 2011

(65) Prior Publication Data

US 2012/0010447 A1 Jan. 12, 2012

Related U.S. Application Data

(60) Provisional application No. 61/363,109, filed on Jul. 9, 2010.

(51) Int. Cl.
*C07C 27/04* (2006.01)

(52) U.S. Cl.
USPC .......................................... 568/884; 568/885

(58) Field of Classification Search
USPC .................................................. 568/884, 885
See application file for complete search history.

(56) References Cited

U.S. PATENT DOCUMENTS

| | | |
|---|---|---|
| 3,130,007 A | 4/1964 | Breck |
| 4,275,228 A | 6/1981 | Gruffaz |
| 4,306,942 A | 12/1981 | Brush |
| 4,317,918 A | 3/1982 | Takano |
| 4,319,058 A | 3/1982 | Kulprathipanja |
| 4,379,028 A | 4/1983 | Berg |
| 4,395,576 A | 7/1983 | Kwantes |
| 4,398,039 A | 8/1983 | Pesa |
| 4,421,939 A | 12/1983 | Kiff |
| 4,422,903 A | 12/1983 | Messick |
| 4,454,358 A | 6/1984 | Kummer |
| 4,465,854 A | 8/1984 | Pond |
| 4,471,136 A | 9/1984 | Larkins |
| 4,480,115 A | 10/1984 | McGinnis |
| 4,492,808 A | 1/1985 | Hagen |
| 4,497,967 A | 2/1985 | Wan |
| 4,520,213 A | 5/1985 | Victor |
| 4,541,897 A | 9/1985 | Sommer |
| 4,961,826 A | 10/1990 | Grethlein |
| 4,985,572 A | 1/1991 | Kitson |
| 4,990,655 A | 2/1991 | Kitson |
| 4,994,608 A | 2/1991 | Torrence |
| 5,001,259 A | 3/1991 | Smith |
| 5,026,908 A | 6/1991 | Smith |
| 5,035,776 A | 7/1991 | Knapp |
| 5,061,671 A | 10/1991 | Kitson |
| 5,124,004 A | 6/1992 | Grethlein |
| 5,144,068 A | 9/1992 | Smith |
| 5,149,680 A | 9/1992 | Kitson |
| 5,185,481 A | 2/1993 | Muto |
| 5,215,902 A | 6/1993 | Tedder |
| 5,227,141 A | 7/1993 | Kim |
| 5,233,099 A | 8/1993 | Tabata |
| 5,237,108 A | 8/1993 | Marraccini |
| 5,250,271 A | 10/1993 | Horizoe |
| 5,348,625 A | 9/1994 | Berg |
| 5,415,741 A | 5/1995 | Berg |
| 5,437,770 A | 8/1995 | Berg |
| 5,445,716 A | 8/1995 | Berg |
| 5,449,440 A | 9/1995 | Rescalli |
| RE35,377 E | 11/1996 | Steinberg |
| 5,599,976 A | 2/1997 | Scates |
| 5,770,770 A | 6/1998 | Kim |
| 5,821,111 A | 10/1998 | Grady |
| 6,121,498 A | 9/2000 | Tustin |
| 6,143,930 A | 11/2000 | Singh |
| 6,232,352 B1 | 5/2001 | Vidalin |
| 6,294,703 B1 | 9/2001 | Hara |
| 6,375,807 B1 | 4/2002 | Nieuwoudt |
| 6,509,180 B1 | 1/2003 | Verser |
| 6,627,770 B1 | 9/2003 | Cheung |
| 6,657,078 B2 | 12/2003 | Scates |
| 6,685,754 B2 | 2/2004 | Kindig |
| 6,693,213 B1 | 2/2004 | Kolena |
| 6,723,886 B2 | 4/2004 | Allison |
| 6,906,228 B2 | 6/2005 | Fischer |
| 6,927,048 B2 | 8/2005 | Verser |
| 7,005,541 B2 | 2/2006 | Cheung |
| 7,074,603 B2 | 7/2006 | Verser |
| 7,115,772 B2 | 10/2006 | Picard |
| 7,208,624 B2 | 4/2007 | Scates |
| 7,297,236 B1 | 11/2007 | Vander Griend |
| 7,351,559 B2 | 4/2008 | Verser |
| 7,507,562 B2 | 3/2009 | Verser |
| 7,553,397 B1 | 6/2009 | Colley |
| 7,572,353 B1 | 8/2009 | Vander Griend |
| 7,601,865 B2 | 10/2009 | Verser |
| 7,608,744 B1 | 10/2009 | Johnston |

(Continued)

FOREIGN PATENT DOCUMENTS

| | | |
|---|---|---|
| EP | 0137749 | 4/1985 |
| EP | 1614458 | 1/2006 |

(Continued)

OTHER PUBLICATIONS

International Preliminary Report on Patentability for PCT/US2011/042784 mailed Oct. 22, 2012.

(Continued)

*Primary Examiner* — Sikarl Witherspoon

(57) ABSTRACT

Recovery of ethanol from a crude ethanol product obtained from the hydrogenation of acetic acid and recovery of unreacted acetic acid from a weak acid stream. The unreacted acetic acid may be recovered as a dry acetic acid composition and may be directly or indirectly fed to the hydrogenation reactor.

25 Claims, 3 Drawing Sheets

(56) References Cited

U.S. PATENT DOCUMENTS

| | | |
|---|---|---|
| 7,682,812 B2 | 3/2010 | Verser |
| 7,744,727 B2 | 6/2010 | Blum |
| 7,884,253 B2 | 2/2011 | Stites |
| 7,888,082 B2 | 2/2011 | Verser |
| 2006/0019360 A1 | 1/2006 | Verser |
| 2006/0127999 A1 | 6/2006 | Verser |
| 2007/0270511 A1 | 11/2007 | Melnichuk |
| 2008/0135396 A1 | 6/2008 | Blum |
| 2008/0193989 A1 | 8/2008 | Verser |
| 2009/0014313 A1 | 1/2009 | Lee |
| 2009/0023192 A1 | 1/2009 | Verser |
| 2009/0069609 A1 | 3/2009 | Kharas |
| 2009/0081749 A1 | 3/2009 | Verser |
| 2009/0166172 A1 | 7/2009 | Casey |
| 2009/0281354 A1 | 11/2009 | Mariansky |
| 2009/0318573 A1 | 12/2009 | Stites |
| 2010/0029980 A1 | 2/2010 | Johnston |
| 2010/0029995 A1 | 2/2010 | Johnston |
| 2010/0030001 A1 | 2/2010 | Chen |
| 2010/0030002 A1 | 2/2010 | Johnston |
| 2010/0121114 A1 | 5/2010 | Weiner |

FOREIGN PATENT DOCUMENTS

| | | |
|---|---|---|
| EP | 2060553 | 5/2009 |
| EP | 2060555 | 5/2009 |
| EP | 2072487 | 6/2009 |
| EP | 2072488 | 6/2009 |
| EP | 2072489 | 6/2009 |
| EP | 2072492 | 6/2009 |
| EP | 2186787 | 5/2010 |
| WO | 8303409 | 10/1983 |
| WO | 2008135192 | 11/2008 |
| WO | 2009009322 | 1/2009 |
| WO | 2009009323 | 1/2009 |
| WO | 2009048335 | 4/2009 |
| WO | 2009063176 | 5/2009 |
| WO | 2010055285 | 5/2010 |

OTHER PUBLICATIONS

International Preliminary Report on Patentability for PCT/US2011/043310 mailed Oct. 22, 2012.

International Search Report and Written Opinion for PCT/US2011/042784 mailed Dec. 7, 2011.

Written Opinion for PCT/US2011/042784 mailed Jul. 16, 2012.

WEAK ACID RECOVERY SYSTEM FOR ETHANOL SEPARATION PROCESSES

CROSS REFERENCE TO RELATED APPLICATIONS

This application claims priority to U.S. App. No. 61/363,109, filed Jul. 9, 2010, the priority of which is hereby claimed and the entirety of which is incorporated herein by reference.

FIELD OF THE INVENTION

The present invention relates generally to processes and systems for producing ethanol and, in particular, to processes and systems for recovering unreacted acetic acid in an ethanol production system.

BACKGROUND OF THE INVENTION

Ethanol for industrial use is conventionally produced from petrochemical feed stocks, such as oil, natural gas, or coal, from feed stock intermediates, such as syngas, or from starchy materials or cellulose materials, such as corn or sugar cane. Conventional methods for producing ethanol from petrochemical feed stocks, as well as from cellulose materials, include the acid-catalyzed hydration of ethylene, methanol homologation, direct alcohol synthesis, and Fischer-Tropsch synthesis. Instability in petrochemical feed stock prices contributes to fluctuations in the cost of conventionally produced ethanol, making the need for alternative sources of ethanol production all the greater when feed stock prices rise. Starchy materials, as well as cellulose material, are converted to ethanol by fermentation. However, fermentation is typically used for consumer production of ethanol for fuels or consumption, which is suitable for fuels or human consumption. In addition, fermentation of starchy or cellulose materials competes with food sources and places restraints on the amount of ethanol that can be produced for industrial use.

Ethanol production via the reduction of alkanoic acids and/or other carbonyl group-containing compounds has been widely studied, and a variety of combinations of catalysts, supports, and operating conditions have been mentioned in the literature. During the reduction of alkanoic acid, e.g., acetic acid, other compounds are formed with ethanol or are formed in side reactions. These impurities limit the production and recovery of ethanol from such reaction mixtures. For example, during hydrogenation, esters are produced that together with ethanol and/or water form azeotropes, which are difficult to separate. In addition when conversion is incomplete, unreacted acetic acid remains in the crude ethanol product, which must be removed to recover ethanol.

EP02060553 describes a process for converting hydrocarbons to ethanol involving converting the hydrocarbons to ethanoic acid and hydrogenating the ethanoic acid to ethanol. The stream from the hydrogenation reactor is separated to obtain an ethanol stream and a stream of acetic acid and ethyl acetate, which is recycled to the hydrogenation reactor.

Therefore, a need remains for improving the recovery of ethanol from a crude product obtained by reducing alkanoic acids, such as acetic acid, and/or other carbonyl group-containing compounds.

SUMMARY OF THE INVENTION

In a first embodiment, the present invention is directed to a process for producing ethanol, comprising the steps of hydrogenating acetic acid in a reactor in the presence of a catalyst to form a crude ethanol product comprising ethanol, water and acetic acid, separating at least a portion of the crude ethanol product in a first column into a first distillate comprising ethanol, and a first residue comprising water and unreacted acetic acid, separating at least a portion of the first residue in a separator column into a separated distillate comprising water, and a separated residue comprising acetic acid, and returning at least a portion of the separated residue to the reactor.

In a second embodiment, the present invention is directed to a process for producing ethanol, comprising the steps of providing a crude ethanol product comprising ethanol, acetic acid, water and ethyl acetate, separating at least a portion of the crude ethanol product in a first column into a first distillate comprising ethanol, and a first residue comprising water and acetic acid, separating at least a portion of the first residue in a separator column into a separated distillate comprising water, and a separated residue comprising acetic acid, and directing at least a portion of the separated residue to an ethanol synthesis reactor. In other embodiments, a portion of the separated residue, which comprises acetic acid, may be directed to a vinyl acetate production process, acetic anhydride production process, or sold separately as a product.

In a third embodiment, the present invention is directed to a process for producing ethanol, comprising the steps of hydrogenating acetic acid in a reactor in the presence of a catalyst to form a crude ethanol product, separating at least a portion of the crude ethanol product in a first column into a first distillate comprising ethanol, ethyl acetate, and less than 10 wt. % water, and a first residue comprising acetic acid and water, and separating at least a portion of the first distillate in a second column into a second distillate comprising ethyl acetate and a second residue comprising ethanol.

BRIEF DESCRIPTION OF DRAWINGS

The invention may be more completely understood in consideration of the following detailed description of various embodiments of the invention in connection with the accompanying drawings, wherein like numerals designate similar parts.

DETAILED DESCRIPTION OF THE INVENTION

Introduction

Figure 1:
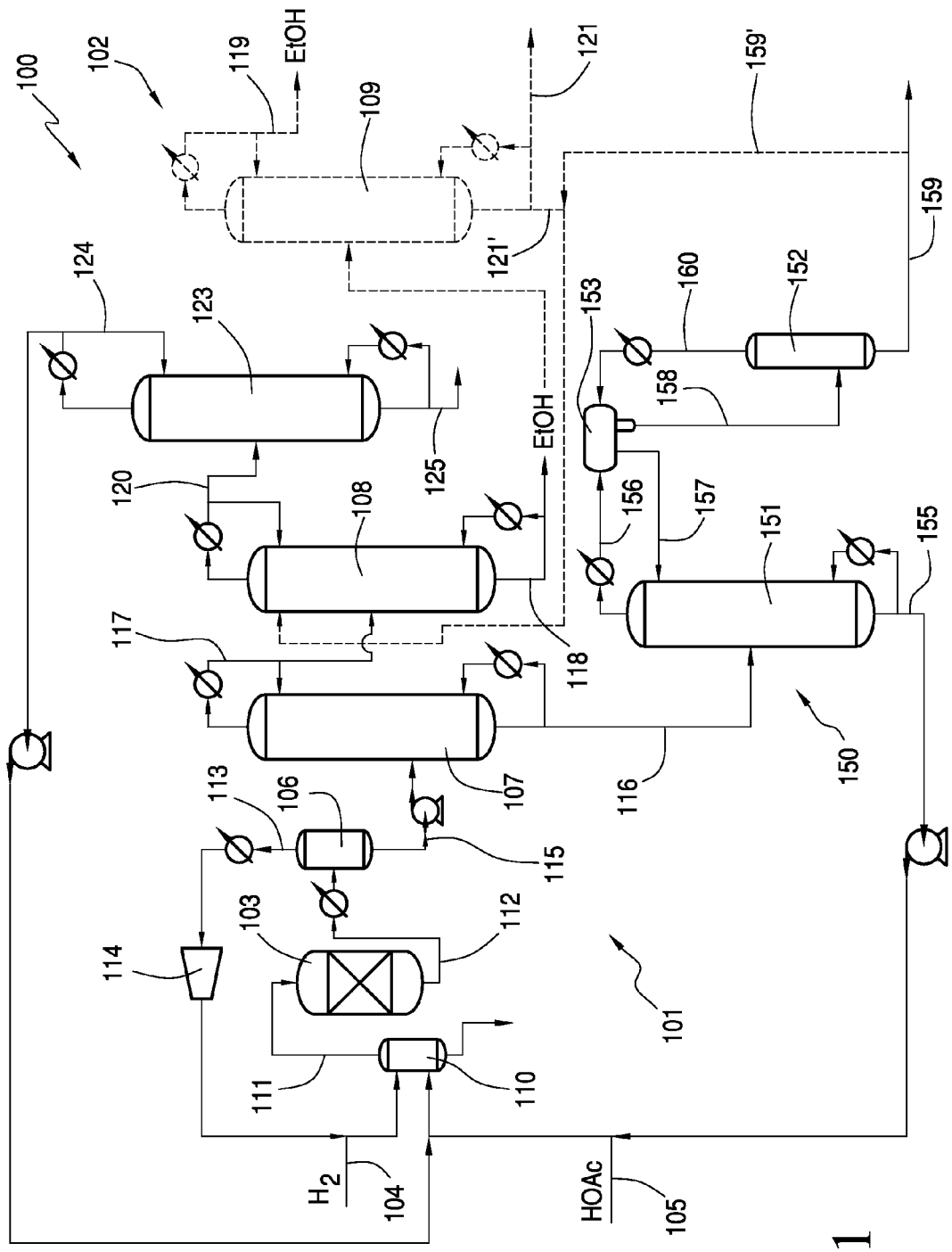
FIG. 1 is a schematic diagram of an ethanol production system and weak acid recovery system in accordance with one embodiment of the present invention.

The present invention relates generally to ethanol production processes and systems for purifying a crude ethanol product and recovering unreacted acetic acid from a weak acid stream. The weak acid stream comprises acetic acid and water and may be obtained from one or more distillation columns used to process a crude ethanol product. The process of the present invention can be applied to a variety of ethanol production systems and beneficially may be used in applications for the recovery and/or purification of ethanol on an industrial scale. For example, various aspects of the present invention relate to processes for recovering and/or purifying ethanol produced by a process comprising hydrogenating acetic acid in the presence of a catalyst.

The hydrogenation reaction produces a crude ethanol product that comprises ethanol, water, ethyl acetate, unreacted acetic acid, and other impurities. To improve operating efficiencies, the processes of the present invention involve separating the crude ethanol product into a weak acid stream and an ethanol product stream. Advantageously, this separation approach results in reducing energy requirements to recover ethanol from the crude ethanol product.

In recovering ethanol, the processes of the present invention use one or more distillation columns. Unreacted acetic acid is removed from the crude ethanol product in the initial (first) column to reduce esterification that would consume the desired ethanol product. In preferred embodiments, the weak acid stream, e.g., residue, comprises a substantial portion of the water and the unreacted acetic acid from the crude ethanol product. Preferably, a majority of the water in the crude ethanol product that is fed to the column is removed as the weak acid stream. The percentage of water removed may vary depending on acetic acid conversion and selectivity, and the weak acid stream, for example, may comprise up to about 90% of the water from the crude ethanol product, and more preferably up to about 75%. In one embodiment, the weak acid stream may comprise from 50% to 90% of the water from the crude ethanol product, and more preferably 55% to 88%, or 63% to 85%. In some embodiments, with lower conversions of acetic acid and/or selectivity, the substantial portion of water withdrawn as in the weak acid stream may be from 30% to 95%, e.g., from 40% to 70%. The percentage of water removed may vary provided that the water concentration in the distillate is greater than the azeotropic amount of water for the distillate.

The weak acid stream may comprise at least 85% of the acetic acid from the crude ethanol product, e.g., at least 90% and more preferably at least about 100%. In terms of ranges, the weak acid stream preferably comprises from 85% to 100% of the unreacted acetic acid from the crude ethanol product, and more preferably from 90% to 100%. In one embodiment, substantially all of the unreacted acetic acid is recovered in the weak acid stream. By removing substantially all of the unreacted acetic acid from the crude ethanol product, the process, in some aspects, does not require further separation of acetic acid from the ethanol. In this aspect, the ethanol product may contain some acetic acid, e.g., trace amounts of acetic acid.

By removing a weak acid stream, which has relatively large portion of the water, from the crude ethanol product in the initial column, in one embodiment, the process beneficially reduces the energy required for further additional water removal steps since less water will be contained in the ethanol-containing distillate of the initial column. Nonetheless, additional water removal steps may be employed in the processes of the invention, for example, if an anhydrous ethanol product is desired. The amount of water in the final ethanol product may vary depending on application, but generally it is advantageous to have an efficient and less costly method for removing water from ethanol.

The process invention recovers acetic acid from the weak acid stream. Preferably the recovered acetic acid is returned to the reactor to increase ethanol production. The water from the weak acid stream may be purged from the system.

Hydrogenation of Acetic Acid

The hydrogenation of acetic acid to form ethanol and water may be represented by the following reaction:

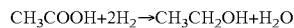

Based on the stoichiometry of the acetic acid hydrogenation reaction, when acetic acid is hydrogenated to form ethanol, the resulting crude ethanol product typically comprises water and ethanol in about a 1:1 mole ratio. Since the conversion to this reaction is less than 100%, however, the crude ethanol product also typically comprises some residual acetic acid.

In one embodiment of the present invention, the process advantageously separates acetic acid and water in a weak acid stream in a single distillation column. Preferably, the temperature at the base of the distillation column is less than the temperature needed to separate acetic acid. The weak acid stream may be returned to the reactor, but it is preferred to remove at least a portion of the water from the weak acid stream before returning the acetic acid to the reactor. Removing water from any return streams to the reactor maintains efficient reaction conditions and reduces unnecessary water processing.

Suitable hydrogenation catalysts include catalysts comprising a first metal and optionally one or more of a second metal, a third metal or additional metals, optionally on a catalyst support. The first and optional second and third metals may be selected from Group IB, IIB, IIIB, IVB, VB, VIIB, VIIB, VIII transition metals, a lanthanide metal, an actinide metal or a metal selected from any of Groups IIIA, IVA, VA, and VIA. Preferred metal combinations for some exemplary catalyst compositions include platinum/tin, platinum/ruthenium, platinum/rhenium, palladium/ruthenium, palladium/rhenium, cobalt/palladium, cobalt/platinum, cobalt/chromium, cobalt/ruthenium, cobalt/tin, silver/palladium, copper/palladium, copper/zinc, nickel/palladium, gold/palladium, ruthenium/rhenium, and ruthenium/iron. Exemplary catalysts are further described in U.S. Pat. No. 7,608,744 and U.S. Pub. No. 2010/0029995, the entireties of which are incorporated herein by reference. In another embodiment, the catalyst comprises a Co/Mo/S catalyst of the type described in U.S. Pub. No. 2009/0069609, the entirety of which is incorporated herein by reference.

In one exemplary embodiment, the catalyst comprises a first metal selected from the group consisting of copper, iron, cobalt, nickel, ruthenium, rhodium, palladium, osmium, iridium, platinum, titanium, zinc, chromium, rhenium, molybdenum, and tungsten. Preferably, the first metal is selected from the group consisting of platinum, palladium, cobalt, nickel, and ruthenium. More preferably, the first metal is selected from platinum and palladium. When the first metal comprises platinum, it is preferred that the catalyst comprises platinum in an amount less than 5 wt. %, e.g., less than 3 wt. % or less than 1 wt. %, due to the high demand for platinum.

As indicated above, the catalyst optionally further comprises a second metal, which typically would function as a promoter. If present, the second metal preferably is selected from the group consisting of copper, molybdenum, tin, chromium, iron, cobalt, vanadium, tungsten, palladium, platinum, lanthanum, cerium, manganese, ruthenium, rhenium, gold, and nickel. More preferably, the second metal is selected from the group consisting of copper, tin, cobalt, rhenium, and nickel. More preferably, the second metal is selected from tin and rhenium.

If the catalyst includes two or more metals, e.g., a first metal and a second metal, the first metal optionally is present in the catalyst in an amount from 0.1 to 10 wt. %, e.g., from 0.1 to 5 wt. %, or from 0.1 to 3 wt. %. The second metal preferably is present in an amount from 0.1 to 20 wt. %, e.g., from 0.1 to 10 wt. %, or from 0.1 to 5 wt. %. For catalysts comprising two or more metals, the two or more metals may be alloyed with one another or may comprise a non-alloyed metal solution or mixture.

The preferred metal ratios may vary depending on the metals used in the catalyst. In some exemplary embodiments, the mole ratio of the first metal to the second metal is from 10:1 to 1:10, e.g., from 4:1 to 1:4, from 2:1 to 1:2, from 1.5:1 to 1:1.5 or from 1.1:1 to 1:1.1.

The catalyst may also comprise a third metal selected from any of the metals listed above in connection with the first or second metal, so long as the third metal is different from the first and second metals. In preferred aspects, the third metal is selected from the group consisting of cobalt, palladium, ruthenium, copper, zinc, platinum, tin, and rhenium. More preferably, the third metal is selected from cobalt, palladium, and ruthenium. When present, the total weight of the third metal preferably is from 0.05 to 4 wt. %, e.g., from 0.1 to 3 wt. %, or from 0.1 to 2 wt. %.

In addition to one or more metals, the exemplary catalysts further comprise a support or a modified support, meaning a support that includes a support material and a support modifier, which adjusts the acidity of the support material. The total weight of the support or modified support, based on the total weight of the catalyst, preferably is from 75 wt. % to 99.9 wt. %, e.g., from 78 wt. % to 97 wt. %, or from 80 wt. % to 95 wt. %. In preferred embodiments that use a modified support, the support modifier is present in an amount from 0.1 wt. % to 50 wt. %, e.g., from 0.2 wt. % to 25 wt. %, from 0.5 wt. % to 15 wt. %, or from 1 wt. % to 8 wt. %, based on the total weight of the catalyst.

Suitable support materials may include, for example, stable metal oxide-based supports or ceramic-based supports. Preferred supports include silicaceous supports, such as silica, silica/alumina, a Group IIA silicate such as calcium metasilicate, pyrogenic silica, high purity silica, and mixtures thereof. Other supports may include, but are not limited to, iron oxide, alumina, titania, zirconia, magnesium oxide, carbon, graphite, high surface area graphitized carbon, activated carbons, and mixtures thereof.

As indicated, the catalyst support may be modified with a support modifier. In some embodiments, the support modifier may be an acidic modifier that increases the acidity of the catalyst. Suitable acidic support modifiers may be selected from the group consisting of: oxides of Group IVB metals, oxides of Group VB metals, oxides of Group VIB metals, oxides of Group VIIB metals, oxides of Group VIIIB metals, aluminum oxides, and mixtures thereof. Acidic support modifiers include those selected from the group consisting of $TiO_2$, $ZrO_2$, $Nb_2O_5$, $Ta_2O_5$, $Al_2O_3$, $B_2O_3$, $P_2O_5$, and $Sb_2O_3$. Preferred acidic support modifiers include those selected from the group consisting of $TiO_2$, $ZrO_2$, $Nb_2O_5$, $Ta_2O_5$, and $Al_2O_3$. The acidic modifier may also include $WO_3$, $MoO_3$, $Fe_2O_3$, $Cr_2O_3$, $V_2O_5$, $MnO_2$, $CuO$, $Co_2O_3$, and $Bi_2O_3$.

In another embodiment, the support modifier may be a basic modifier that has a low volatility or no volatility. Such basic modifiers, for example, may be selected from the group consisting of: (i) alkaline earth oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. In addition to oxides and metasilicates, other types of modifiers including nitrates, nitrites, acetates, and lactates may be used. Preferably, the support modifier is selected from the group consisting of oxides and metasilicates of any of sodium, potassium, magnesium, calcium, scandium, yttrium, and zinc, as well as mixtures of any of the foregoing. More preferably, the basic support modifier is a calcium silicate, and even more preferably calcium metasilicate ($CaSiO_3$). If the basic support modifier comprises calcium metasilicate, it is preferred that at least a portion of the calcium metasilicate is in crystalline form.

A preferred silica support material is SS61138 High Surface Area (HSA) Silica Catalyst Carrier from Saint Gobain N or Pro. The Saint-Gobain N or Pro SS61138 silica exhibits the following properties: contains approximately 95 wt. % high surface area silica; surface area of about 250 m$^2$/g; median pore diameter of about 12 nm; average pore volume of about 1.0 cm$^3$/g as measured by mercury intrusion porosimetry and a packing density of about 0.352 g/cm$^3$ (22 lb/ft$^3$).

A preferred silica/alumina support material is KA-160 silica spheres from Sud Chemie having a nominal diameter of about 5 mm, a density of about 0.562 g/ml, an absorptivity of about 0.583 g $H_2O$/g support, a surface area of about 160 to 175 m$^2$/g, and a pore volume of about 0.68 ml/g.

As will be appreciated by those of ordinary skill in the art, support materials are selected such that the catalyst system is suitably active, selective and robust under the process conditions employed for the formation of ethanol.

The metals of the catalysts may be dispersed throughout the support, coated on the outer surface of the support (egg shell) or decorated on the surface of the support.

The catalyst compositions suitable for use with the present invention preferably are formed through metal impregnation of the modified support, although other processes such as chemical vapor deposition may also be employed. Such impregnation techniques are described in U.S. Pat. No. 7,608,744 and U.S. Pub. No. 2010/0029995, the entireties of which are incorporated herein by reference.

Some embodiments of the process of hydrogenating acetic acid to form ethanol may include a variety of configurations using a fixed bed reactor or a fluidized bed reactor. In many embodiments of the present invention, an "adiabatic" reactor can be used; that is, there is little or no need for internal plumbing through the reaction zone to add or remove heat. In other embodiments, a radial flow reactor or reactors may be employed, or a series of reactors may be employed with or without heat exchange, quenching, or introduction of additional feed material. Alternatively, a shell and tube reactor provided with a heat transfer medium may be used. In many cases, the reaction zone may be housed in a single vessel or in a series of vessels with heat exchangers therebetween.

In preferred embodiments, the catalyst is employed in a fixed bed reactor, e.g., in the shape of a pipe or tube, where the reactants, typically in the vapor form, are passed over or through the catalyst. Other reactors, such as fluid or ebullient bed reactors, can be employed. In some instances, the hydrogenation catalysts may be used in conjunction with an inert material to regulate the pressure drop of the reactant stream through the catalyst bed and the contact time of the reactant compounds with the catalyst particles.

The hydrogenation reaction may be carried out in either the liquid phase or vapor phase. Preferably, the reaction is carried out in the vapor phase under the following conditions. The reaction temperature may range from 125° C. to 350° C., e.g., from 200° C. to 325° C., from 225° C. to 300° C., or from 250° C. to 300° C. The pressure may range from 10 kPa to 3000 kPa, e.g., from 50 kPa to 2300 kPa, or from 100 kPa to 1500 kPa. The reactants may be fed to the reactor at a gas hourly space velocity (GHSV) of greater than 500 hr$^{-1}$, e.g., greater than 1000 hr$^{-1}$, greater than 2500 hr$^{-1}$ or even greater than 5000 hr$^{-1}$. In terms of ranges the GHSV may range from 50 hr$^{-1}$ to 50,000 hr$^{-1}$, e.g., from 500 hr$^{-1}$ to 30,000 hr$^{-1}$, from 1000 hr$^{-1}$ to 10,000 hr$^{-1}$, or from 1000 hr$^{-1}$ to 6500 hr$^{-1}$.

The hydrogenation optionally is carried out at a pressure just sufficient to overcome the pressure drop across the catalytic bed at the GHSV selected, although there is no bar to the use of higher pressures, it being understood that considerable pressure drop through the reactor bed may be experienced at high space velocities, e.g., 5000 hr$^{-1}$ or 6,500 hr$^{-1}$.

Although the reaction consumes two moles of hydrogen per mole of acetic acid to produce one mole of ethanol, the actual molar ratio of hydrogen to acetic acid in the feed stream may vary from about 100:1 to 1:100, e.g., from 50:1 to 1:50, from 20:1 to 1:2, or from 12:1 to 1:1. Most preferably, the molar ratio of hydrogen to acetic acid is greater than 2:1, e.g., greater than 4:1 or greater than 8:1.

Contact or residence time can also vary widely, depending upon such variables as amount of acetic acid, catalyst, reactor, temperature, and pressure. Typical contact times range from a fraction of a second to more than several hours when a catalyst system other than a fixed bed is used, with preferred contact times, at least for vapor phase reactions, of from 0.1 to 100 seconds, e.g., from 0.3 to 80 seconds or from 0.4 to 30 seconds.

The raw materials, acetic acid and hydrogen, used in connection with the process of this invention may be derived from any suitable source including natural gas, petroleum, coal, biomass, and so forth. As examples, acetic acid may be produced via methanol carbonylation, acetaldehyde oxidation, ethylene oxidation, oxidative fermentation, and anaerobic fermentation. Methanol carbonylation processes suitable for production of acetic acid are described in U.S. Pat. Nos. 7,208,624; 7,115,772; 7,005,541; 6,657,078; 6,627,770; 6,143,930; 5,599,976; 5,144,068; 5,026,908; 5,001,259; and 4,994,608, the entire disclosures of which are incorporated herein by reference. Optionally, the production of ethanol may be integrated with such methanol carbonylation processes.

As petroleum and natural gas prices fluctuate becoming either more or less expensive, methods for producing acetic acid and intermediates such as methanol and carbon monoxide from alternate carbon sources have drawn increasing interest. In particular, when petroleum is relatively expensive, it may become advantageous to produce acetic acid from synthesis gas ("syngas") that is derived from more available carbon sources. U.S. Pat. No. 6,232,352, the entirety of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syngas is diverted from the methanol synthesis loop and supplied to a separator unit to recover CO, which is then used to produce acetic acid. In a similar manner, hydrogen for the hydrogenation step may be supplied from syngas.

In some embodiments, some or all of the raw materials for the above-described acetic acid hydrogenation process may be derived partially or entirely from syngas. For example, the acetic acid may be formed from methanol and carbon monoxide, both of which may be derived from syngas. The syngas may be formed by partial oxidation reforming or steam reforming, and the carbon monoxide may be separated from syngas. Similarly, hydrogen that is used in the step of hydrogenating the acetic acid to form the crude ethanol product may be separated from syngas. The syngas, in turn, may be derived from variety of carbon sources. The carbon source, for example, may be selected from the group consisting of natural gas, oil, petroleum, coal, biomass, and combinations thereof. Syngas or hydrogen may also be obtained from bio-derived methane gas, such as bio-derived methane gas produced by landfills or agricultural waste.

In another embodiment, the acetic acid used in the hydrogenation step may be formed from the fermentation of biomass. The fermentation process preferably utilizes an acetogenic process or a homoacetogenic microorganism to ferment sugars to acetic acid producing little, if any, carbon dioxide as a by-product. The carbon efficiency for the fermentation process preferably is greater than 70%, greater than 80% or greater than 90% as compared to conventional yeast processing, which typically has a carbon efficiency of about 67%. Optionally, the microorganism employed in the fermentation process is of a genus selected from the group consisting of *Clostridium, Lactobacillus, Moorella, Thermoanaerobacter, Propionibacterium, Propionispera, Anaerobiospirillum,* and *Bacteriodes,* and in particular, species selected from the group consisting of *Clostridium formicoaceticum, Clostridium butyricum, Moorella thermoacetica, Thermoanaerobacter kivui, Lactobacillus delbrukii, Propionibacterium acidipropionici, Propionispera arboris, Anaerobiospirillum succinicproducens, Bacteriodes amylophilus* and *Bacteriodes ruminicola.* Optionally in this process, all or a portion of the unfermented residue from the biomass, e.g., lignans, may be gasified to form hydrogen that may be used in the hydrogenation step of the present invention. Exemplary fermentation processes for forming acetic acid are disclosed in U.S. Pat. Nos. 6,509,180; 6,927,048; 7,074,603; 7,507,562; 7,351,559; 7,601,865; 7,682,812; and 7,888,082, the entireties of which are incorporated herein by reference. See also U.S. Pub. Nos. 2008/0193989 and 2009/0281354, the entireties of which are incorporated herein by reference.

Examples of biomass include, but are not limited to, agricultural wastes, forest products, grasses, and other cellulosic material, timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. See, e.g., U.S. Pat. No. 7,884,253, the entirety of which is incorporated herein by reference. Another biomass source is black liquor, a thick, dark liquid that is a byproduct of the Kraft process for transforming wood into pulp, which is then dried to make paper. Black liquor is an aqueous solution of lignin residues, hemicellulose, and inorganic chemicals.

U.S. Pat. No. RE 35,377, also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolyzed with additional natural gas to form synthesis gas. The syngas is converted to methanol which may be carbonylated to acetic acid. The method likewise produces hydrogen which may be used in connection with this invention as noted above. U.S. Pat. No. 5,821,111, which discloses a process for converting waste biomass through gasification into synthesis gas, and U.S. Pat. No. 6,685,754, which discloses a method for the production of a hydrogen-containing gas composition, such as a synthesis gas including hydrogen and carbon monoxide, are incorporated herein by reference in their entireties.

In one optional embodiment, the acetic acid fed to the hydrogenation reaction may also comprise other carboxylic acids and anhydrides, as well as acetaldehyde and acetone. These other compounds may also be hydrogenated in the processes of the present invention. In some embodiments, the presence of carboxylic acids, such as propanoic acid or its anhydride, may be beneficial in producing propanol.

Alternatively, acetic acid in vapor form may be taken directly as crude product from the flash vessel of a methanol carbonylation unit of the class described in U.S. Pat. No. 6,657,078, the entirety of which is incorporated herein by reference. The crude vapor product, for example, may be fed directly to the ethanol synthesis reaction zones of the present invention without the need for condensing the acetic acid and light ends or removing water, saving overall processing costs.

The acetic acid may be vaporized at the reaction temperature, following which the vaporized acetic acid may be fed along with hydrogen in an undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid. In one embodiment, the acetic acid may be vaporized at the boiling point of acetic acid at the particular pressure, and then the vaporized acetic acid may be further heated to the reactor inlet temperature. In another embodiment, the acetic acid is mixed with other gases before vaporizing, followed by heating the mixed vapors up to the reactor inlet temperature. Preferably, the acetic acid is transferred to the vapor state by passing hydrogen and/or recycle gas through the acetic acid at a temperature at or below 125° C., followed by heating of the combined gaseous stream to the reactor inlet temperature.

In particular, the hydrogenation of acetic acid may achieve favorable conversion of acetic acid and favorable selectivity and productivity to ethanol. For purposes of the present invention, the term "conversion" refers to the amount of acetic acid in the feed that is converted to a compound other than acetic acid. Conversion is expressed as a mole percentage based on acetic acid in the feed. The conversion may be at least 10%, e.g., at least 20%, at least 40%, at least 50%, at least 60%, at least 70% or at least 80%. Although catalysts that have high conversions are desirable, such as at least 80% or at least 90%, in some embodiments a low conversion may be acceptable at high selectivity for ethanol. It is, of course, well understood that in many cases, it is possible to compensate for conversion by appropriate recycle streams or use of larger reactors, but it is more difficult to compensate for poor selectivity.

Selectivity is expressed as a mole percent based on converted acetic acid. It should be understood that each compound converted from acetic acid has an independent selectivity and that selectivity is independent from conversion. For example, if 60 mole % of the converted acetic acid is converted to ethanol, we refer to the ethanol selectivity as 60%. Preferably, the catalyst selectivity to ethoxylates is at least 60%, e.g., at least 70%, or at least 80%. As used herein, the term "ethoxylates" refers specifically to the compounds ethanol, acetaldehyde, and ethyl acetate. Preferably, the selectivity to ethanol is at least 80%, e.g., at least 85% or at least 88%. Preferred embodiments of the hydrogenation process also have low selectivity to undesirable products, such as methane, ethane, and carbon dioxide. The selectivity to these undesirable products preferably is less than 4%, e.g., less than 2% or less than 1%. More preferably, these undesirable products are not detectable. Formation of alkanes may be low, and ideally less than 2%, less than 1%, or less than 0.5% of the acetic acid passed over the catalyst is converted to alkanes, which have little value other than as fuel.

The term "productivity," as used herein, refers to the grams of a specified product, e.g., ethanol, formed during the hydrogenation based on the kilograms of catalyst used per hour. A productivity of at least 100 grams of ethanol per kilogram of catalyst per hour, e.g., at least 400 grams of ethanol per kilogram of catalyst per hour or at least 600 grams of ethanol per kilogram of catalyst per hour, is preferred. In terms of ranges, the productivity preferably is from 100 to 3,000 grams of ethanol per kilogram of catalyst per hour, e.g., from 400 to 2,500 grams of ethanol per kilogram of catalyst per hour or from 600 to 2,000 grams of ethanol per kilogram of catalyst per hour.

Operating under the conditions of the present invention may result in ethanol production on the order of at least 0.1 tons of ethanol per hour, e.g., at least 1 ton of ethanol per hour, at least 5 tons of ethanol per hour, or at least 10 tons of ethanol per hour. Larger scale industrial production of ethanol, depending on the scale, generally should be at least 1 ton of ethanol per hour, e.g., at least 15 tons of ethanol per hour or at least 30 tons of ethanol per hour. In terms of ranges, for large scale industrial production of ethanol, the process of the present invention may produce from 0.1 to 160 tons of ethanol per hour, e.g., from 15 to 160 tons of ethanol per hour or from 30 to 80 tons of ethanol per hour. Ethanol production from fermentation, due the economies of scale, typically does not permit the single facility ethanol production that may be achievable by employing embodiments of the present invention.

In various embodiments, the crude ethanol product produced by the hydrogenation process, before any subsequent processing, such as purification and separation, will typically comprise unreacted acetic acid, ethanol and water. As used herein, the term "crude ethanol product" refers to any composition comprising from 5 to 70 wt. % ethanol and from 5 to 40 wt. % water. Exemplary compositional ranges for the crude ethanol product are provided in Table 1. The "others" identified in Table 1 may include, for example, esters, ethers, aldehydes, ketones, alkanes, and carbon dioxide.

TABLE 1

CRUDE ETHANOL PRODUCT COMPOSITIONS

| Component | Conc. (wt. %) | Conc. (wt. %) | Conc. (wt. %) | Conc. (wt. %) |
|---|---|---|---|---|
| Ethanol | 5 to 70 | 15 to 70 | 15 to 50 | 25 to 50 |
| Acetic Acid | 0 to 90 | 0 to 50 | 15 to 70 | 20 to 70 |
| Water | 5 to 40 | 5 to 30 | 10 to 30 | 10 to 26 |
| Ethyl Acetate | 0 to 30 | 0 to 20 | 1 to 12 | 3 to 10 |
| Acetaldehyde | 0 to 10 | 0 to 3 | 0.1 to 3 | 0.2 to 2 |
| Others | 0.1 to 10 | 0.1 to 6 | 0.1 to 4 | — |

In one embodiment, the crude ethanol product comprises acetic acid in an amount less than 20 wt. %, e.g., less than 15 wt. %, less than 10 wt. % or less than 5 wt. %. In embodiments having lower amounts of acetic acid, the conversion of acetic acid is preferably greater than 75%, e.g., greater than 85% or greater than 90%. In addition, the selectivity to ethanol may also be preferably high, and is preferably greater than 75%, e.g., greater than 85% or greater than 90%.

Separation of Crude Ethanol

Figure 2:
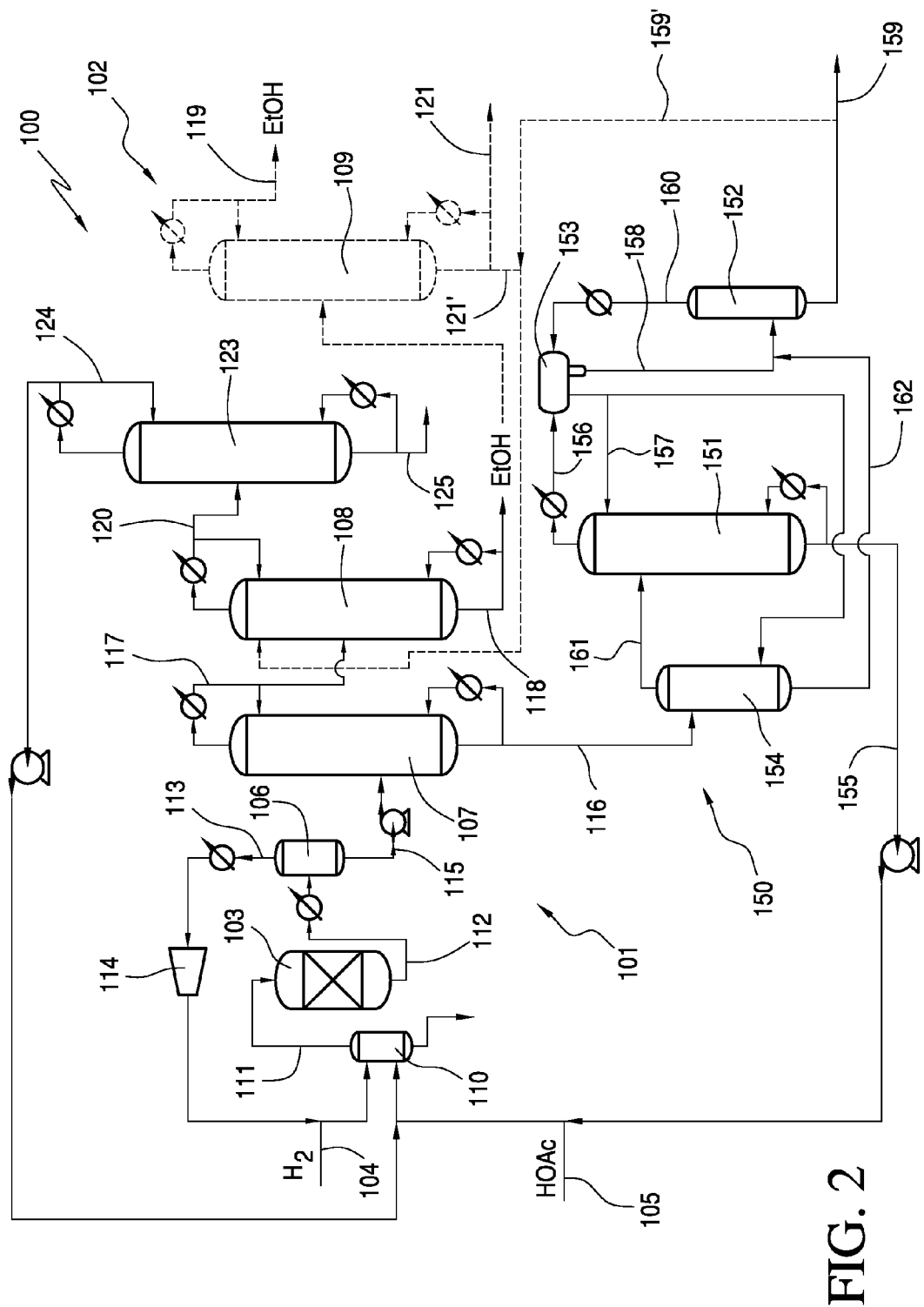
FIG. 2 is a schematic diagram of an ethanol production system and weak acid recovery system having an extractor in accordance with one embodiment of the present invention.
Figure 3:
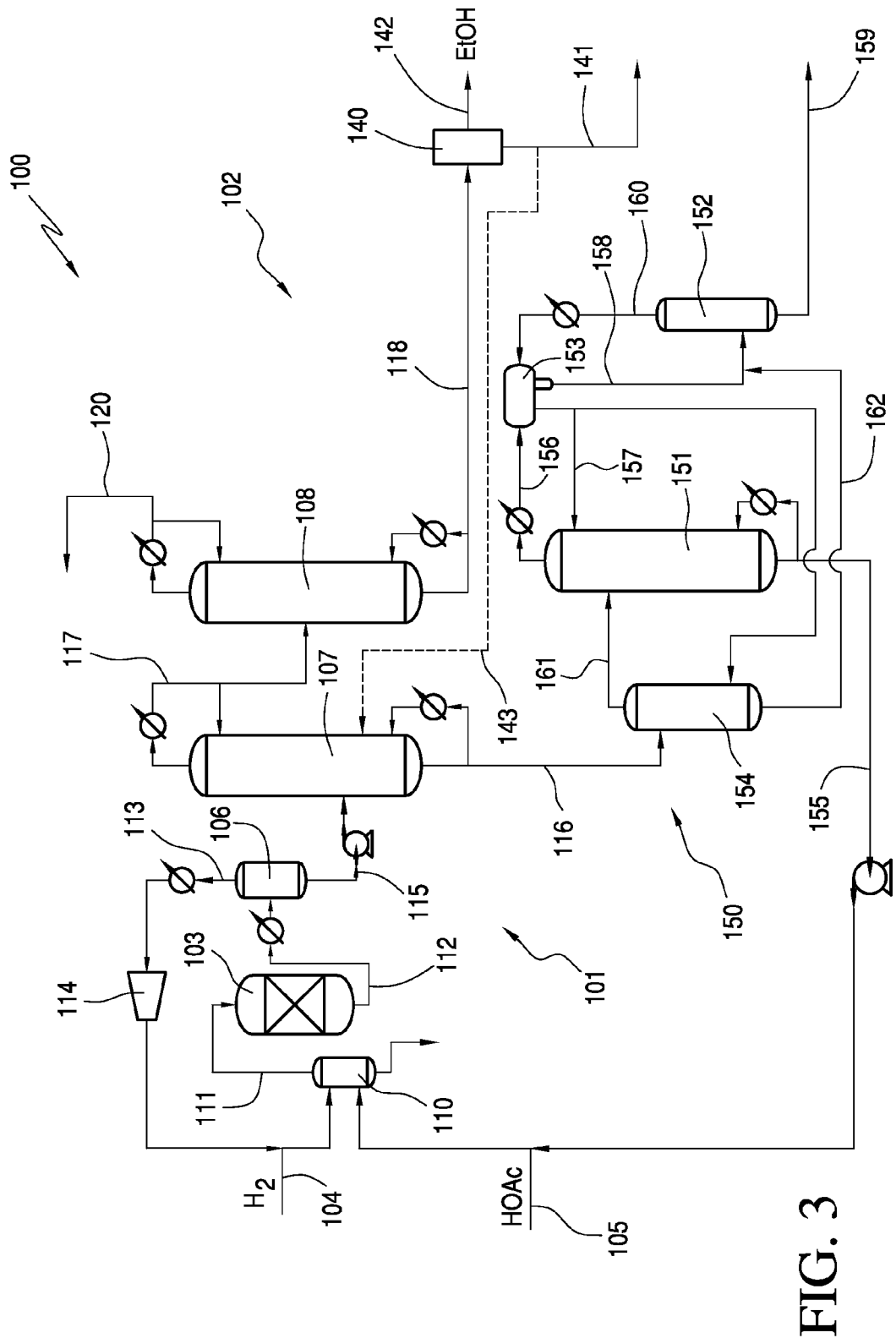
FIG. 3 is a schematic diagram of an ethanol production system having a water separator and weak acid recovery system having an extractor in accordance with one embodiment of the present invention.

FIGS. 1, 2, and 3 show a hydrogenation system 100 suitable for the hydrogenation of acetic acid and separating ethanol from the crude reaction mixture according to one embodiment of the invention. System 100 comprises reaction zone 101, separation zone 102, weak acid recovery zone 150. Reaction zone 101 comprises reactor 103, hydrogen feed line 104 and acetic acid feed line 105. Separation zone 102 comprises flasher 106, first column 107, and second column 108, optional third column 109, and fourth column 123. Weak acid recovery zone 150, in FIG. 1, comprises azeotropic acid-water separator column 151, effluent still 152 and decanter 153. In FIG. 2, the weak acid recovery zone 150 comprises azeotropic acid-water separator column 151, effluent still 152, extractor 154 and decanter 153. Weak acid recovery zone 150 receives an weak acid stream from the separation zone. FIG. 3 shows a weak acid recovery zone 150 similar to FIG. 2, with first column 107, second column 108, and a water separator 140 for recovering ethanol.

In preferred embodiments, when the weak acid stream comprises about 30 wt. % or more of acetic acid, e.g., about 40 wt. % or more, or about 50 wt. % or more, the weak acid stream processed using the weak acid recovery zone shown in FIG. 1. When the weak acid stream comprises less than 60 wt. % acetic acid, e.g., less than 50 wt. % or less than 40 wt. %, the weak acid stream is processed using the weak acid recovery zone shown in FIG. 2. In optional embodiments, the weak acid system as shown may process a weak acid stream containing any amount of acetic acid.

Hydrogen and acetic acid are fed to a vaporizer 110 via lines 104 and 105, respectively, to create a vapor feed stream in line 111 that is directed to reactor 103. In one embodiment, lines 104 and 105 may be combined and jointly fed to the vaporizer 110, e.g., in one stream containing both hydrogen and acetic acid. The temperature of the vapor feed stream in line 111 is preferably from 100° C. to 350° C., e.g., from 120° C. to 310° C. or from 150° C. to 300° C. Any feed that is not vaporized is removed from vaporizer 110, as shown, and may be recycled or discarded. In addition, although FIGS. 1 and 2 represent line 111 being directed to the top of reactor 103, line 111 may be directed to the side, upper portion, or bottom of reactor 103. Further modifications and additional components to reaction zone 101 are described below.

Reactor 103 contains the catalyst that is used in the hydrogenation of the carboxylic acid, preferably acetic acid. In one embodiment, one or more guard beds (not shown) may be used to protect the catalyst from poisons or undesirable impurities contained in the feed or return/recycle streams. Such guard beds may be employed in the vapor or liquid streams. Suitable guard bed materials are known in the art and include, for example, carbon, silica, alumina, ceramic, or resins. In one aspect, the guard bed media is functionalized to trap particular species such as sulfur or halogens. During the hydrogenation process, a crude ethanol product stream is withdrawn, preferably continuously, from reactor 103 via line 112. The crude ethanol product stream may be condensed and fed to flasher 106, which, in turn, provides a vapor stream and a liquid stream. The flasher 106 in one embodiment preferably operates at a temperature of from 20° C. to 250° C., e.g., from 30° C. to 225° C. or from 60° C. to 200° C. In one embodiment, the pressure of flasher 106 preferably is from 50 kPa to 2000 kPa, e.g., from 75 kPa to 1500 kPa, or from 100 kPa to 1000 kPa.

The vapor stream exiting the flasher 106 may comprise hydrogen and hydrocarbons, which may be purged and/or returned to reaction zone 101 via line 113. As shown in FIG. 1, the returned portion of the vapor stream passes through compressor 114 and is combined with the hydrogen feed and co-fed to vaporizer 110.

The liquid from flasher 106 is withdrawn and pumped via line 115 to the side of first column 107, also referred to as the acid separation column. In one embodiment, the contents of line 115 are substantially similar to the crude ethanol product obtained from the reactor, except that the composition has substantially no hydrogen, carbon dioxide, methane or ethane, which are removed by the flasher 106. Exemplary components of liquid in line 115 are provided in Table 2. It should be understood that liquid line 115 may contain other components, not listed, such as components derived from the feed.

TABLE 2

| | FEED COMPOSITION | | |
|---|---|---|---|
| | Conc. (wt. %) | Conc. (wt. %) | Conc. (wt. %) |
| Ethanol | 5 to 70 | 10 to 60 | 15 to 50 |
| Acetic Acid | <90 | 5 to 80 | 15 to 70 |
| Water | 5 to 40 | 5 to 30 | 10 to 30 |
| Ethyl Acetate | <30 | 0.001 to 20 | 1 to 12 |
| Acetaldehyde | <10 | 0.001 to 3 | 0.1 to 3 |
| Acetal | <5 | 0.001 to 2 | 0.005 to 1 |
| Acetone | <5 | 0.0005 to 0.05 | 0.001 to 0.03 |
| Other Esters | <5 | <0.005 | <0.001 |
| Other Ethers | <5 | <0.005 | <0.001 |
| Other Alcohols | <5 | <0.005 | <0.001 |

The amounts indicated as less than (<) in the tables throughout present application are preferably not present and if present may be present in trace amounts or in amounts greater than 0.0001 wt. %.

The "other esters" in Table 2 may include, but are not limited to, ethyl propionate, methyl acetate, isopropyl acetate, n-propyl acetate, n-butyl acetate or mixtures thereof. The "other ethers" in Table 2 may include, but are not limited to, diethyl ether, methyl ethyl ether, isobutyl ethyl ether or mixtures thereof. The "other alcohols" in Table 2 may include, but are not limited to, methanol, isopropanol, n-propanol, n-butanol or mixtures thereof. In one embodiment, the liquid stream 115 may comprise propanol, e.g., isopropanol and/or n-propanol, in an amount from 0.001 to 0.1 wt. %, from 0.001 to 0.05 wt. % or from 0.001 to 0.03 wt. %. In should be understood that these other components may be carried through in any of the distillate or residue streams described herein and will not be further described herein, unless indicated otherwise.

When the content of acetic acid in liquid stream 115 is less than 5 wt. %, the acid separation column 107 may be skipped and liquid stream 115 may be introduced directly to second column 108, also referred to as the light ends column. In addition, column 107 may be operated to initially remove a substantial portion of water as the residue.

In one embodiment, line 115 is introduced in the lower part of first column 107, e.g., lower half or lower third. In first column 107, unreacted acetic acid, a portion of the water, and other heavy components, if present, are removed from the composition in line 115 and are withdrawn, preferably continuously, as residue to form a weak acid stream in line 116. The composition of weak acid stream may vary, but preferably comprises acetic acid and water. Other components of weak acid stream are described in Table 3 below. In embodiments of the present invention, weak acid stream in line 116 may be processed in a weak acid recovery zone 150 before being returned to the reaction zone. Optionally, a portion of the weak acid stream may be returned directly to the reaction zone 101 without being processed in the weak acid recovery zone 150. Recycling the acetic acid preferably from the weak acid recovery zone 150 to the vaporizer 110 may reduce the amount of heavies that need to be purged from vaporizer 110. Reducing the amount of heavies to be purged may improve efficiencies of the process while reducing byproducts.

Weak Acid Recovery

In FIG. 1, weak acid stream 116 is introduced in the middle section of the azeotropic acid-water separator column 151, and optionally in the lower part of column 151. Generally it is difficult to separate mixtures of acetic acid in water, even though acetic acid does not form an azeotrope with water. In one embodiment, separator column 151 may comprise an extraction agent, such as an compound capable of forming an azeotrope with water. The compound preferably does not form an azeotrope with acetic acid. Suitable azeotrope compounds include ethyl acetate, propyl acetate, isopropyl acetate, butyl acetate, vinyl acetate, diisopropyl ether, carbon disulfide, tetrahydrofuran, isopropanol, ethanol, and $C_3$-$C_{12}$ alkanes. Ethyl acetate, isopropyl acetate and diisopropyl ether are preferred azeotrope compounds. Ethyl acetate is a preferred azeotrope compound that may be obtained from one or more derivative streams in the system 100, such as the residue in line 125 of fourth column 123. The azeotrope with water preferred has a boiling point that is lower than acetic acid (118° C.) and may be separated from the acetic acid in separator column 151.

When separator column 151 is operated under standard atmospheric pressure, the temperature of the residue exiting in line 155 from column 151 preferably is from 100° C. to 160° C., e.g., from 105° C. to 150° C. or from 130° C. to 145° C. The temperature of the distillate exiting in line 156 from column 151 preferably is from 70° C. to 95° C., e.g., from 75° C. to 90° C. or from 80° C. to 90° C. In other embodiments, the pressure of separator column 151 may range from 0.1 kPa to 510 kPa, e.g., from 1 kPa to 475 kPa or from 1 kPa to 375 kPa.

The acetic acid is withdrawn from the separator column 151 as the residue in line 155 and directed to the reaction zone 101. The composition of the residue in line 155 is essentially acetic acid in an amount of greater than 80 wt. %, e.g., greater than 90 wt. %. greater than 97 wt. %, greater than 98.5 wt. % or greater than 99 wt. %. In one embodiment, the amount of water in residue 155 is less than 3 wt. %, e.g., less than 1 wt. % or less than 0.5 wt. %. In preferred embodiments, the acetic acid concentration of residue in line 155 is greater than the acetic acid concentration of residue in line 116.

In one embodiment, the residue in line 155 may be fed to an ethanol synthesis reactor, such as the hydrogenation reactor 103 shown in FIG. 1. In other embodiments, a portion of the separated residue, which comprises acetic acid, may be directed to a vinyl acetate production process, acetic anhydride production process, or sold separately as a product.

The distillate in line 156 of separator column 151 comprises the water azeotrope and may be condensed and fed to a decanter 153. Decanter 153 biphasically separates the distillate into a light phase in line 157 that comprises azeotrope compound, preferably ethyl acetate, and a heavy phase in line 158 that comprises water. The light phase in line 157 may be in total reflux as shown in FIG. 1, or is partially refluxed to separator column 151 while another portion is purged from the system 100. The heavy phase in line 158 is fed to effluent still 152 to recover an effluent stream comprising water in line 159 and a vapor stream comprising the azeotrope compound, i.e., ethyl acetate, in line 160. When still 152 is operated under standard atmospheric pressure, the temperature of the effluent exiting in line 159 preferably is from 100° C. to 120° C., e.g., from 105° C. to 115° C. or from 105° C. to 110° C. The temperature of the vapor overheads exiting in line 160 from still 152 preferably is from 70° C. to 95° C., e.g., from 75° C. to 90° C. or from 80° C. to 89° C. The vapor overhead in line 160 may be condensed and directly or indirectly fed to the decanter 153. Effluent stream 159 may be purged from the system, or optionally introduced to an extraction distillation column, such as the second column 108.

Weak acid stream 116 that is fed to weak acid recovery zone 150 in FIG. 1 preferably comprises acetic acid in an amount of about 30 wt. % or more of acetic acid, e.g., about 40 wt. % or more, or about 50 wt. % or more. In embodiments when weak acid stream 116 comprises less than less than 60 wt. % acetic acid, e.g., less than 50 wt. % or less than 40 wt.

%, a weak acid recovery zone 150 as shown in FIG. 2 may be used. Weak acid stream 116 is initially introduced to the upper portion of an extractor 154. Extractor 154 may also receive a portion of the light phase 157 from decanter 153, which comprises an azeotrope compound, preferably ethyl acetate, suitable for extraction. The extract in line 161 of extractor 154 are fed to the separator column 151. When extractor 154 is operated under standard atmospheric pressure, the temperature of the raffinate exiting in line 162 and the extract exiting in line 161 preferably are from 40° C. to 110° C., e.g., from 40° C. to 100° C. or from 45° C. to 95° C.

In one embodiment, the amount of water in the extract in line 161 is less than the amount of water in weak acid stream 116. Preferably the extract in line 161 comprises at least 10 wt. % acetic acid, e.g., 25 wt. % acetic acid or at least 50 wt. % acetic acid. The raffinate in line 162 of the extractor 154, which comprises water and the azeotrope compound, are directed to the effluent still 152. Separator column 151 operates as described above in FIG. 1.

Ethanol Recovery

Returning to the separation zone 102, first column 107 also forms an overhead distillate, which is withdrawn in line 117, and which may be condensed and refluxed, for example, at a ratio of from 10:1 to 1:10, e.g., from 3:1 to 1:3 or from 1:2 to 2:1.

When first column 107 is operated under about 170 kPa, the temperature of the residue exiting in line 116 from column 107 preferably is from 90° C. to 130° C., e.g., from 95° C. to 120° C. or from 100° C. to 115° C. The temperature of the distillate exiting in line 117 from column 107 preferably is from 60° C. to 90° C., e.g., from 65° C. to 85° C. or from 70° C. to 80° C. In preferred embodiments, the distillate in line 117 comprises one or more binary and tertiary azeotropes of water, ethanol, and/or ethyl acetate and the temperature of the distillate in line 117 may be approximately at or above the boiling points of any of these azeotropes. The one or more binary and tertiary azeotropes of water, ethanol, and/or ethyl acetate include water/ethanol, water/ethyl acetate, ethanol/ ethyl acetate and water/ethanol/ethyl acetate. In other embodiments, the pressure of first column 107 may range from 0.1 kPa to 510 kPa, e.g., from 1 kPa to 475 kPa or from 1 kPa to 375 kPa. Exemplary components of the distillate and residue compositions for first column 107 are provided in Table 3 below. It should be understood that the distillate and residue may also contain other components, not listed, such as components derived from the feed. For convenience, the distillate and residue of the first column may also be referred to as the "first distillate" or "first residue." The distillates or residues of the other columns may also be referred to with similar numeric modifiers (second, third, etc.) in order to distinguish them from one another, but such modifiers should not be construed as requiring any particular separation order.

TABLE 3

| | FIRST COLUMN | | |
|---|---|---|---|
| | Conc. (wt. %) | Conc. (wt. %) | Conc. (wt. %) |
| Distillate | | | |
| Ethanol | 20 to 75 | 30 to 70 | 40 to 65 |
| Water | <40 | 1 to 35 | 5 to 35 |
| Acetic Acid | <2 | 0.001 to 0.5 | 0.01 to 0.2 |
| Ethyl Acetate | <60 | 5.0 to 40 | 10 to 30 |
| Acetaldehyde | <10 | 0.001 to 5 | 0.01 to 4 |

TABLE 3-continued

FIRST COLUMN

|  | Conc. (wt. %) | Conc. (wt. %) | Conc. (wt. %) |
|---|---|---|---|
| Acetal | <0.1 | <0.1 | <0.05 |
| Acetone | <0.05 | 0.001 to 0.03 | 0.01 to 0.025 |
| Residue |  |  |  |
| Acetic Acid | 5 to 100 | 10 to 90 | 25 to 75 |
| Water | <95 | 10 to 90 | 25 to 75 |
| Ethanol | <1 | <0.9 | <0.07 |

In one embodiment, the amount of water in the distillate may be less than the amount of water in the binary and/or tertiary azeotropes of water, ethanol and/or ethyl acetate. In terms of wt. %, the amount of water in the distillate is less than 10 wt. %, e.g., less than 9 wt. % or less than 8 wt. %. In one embodiment the amount of water in the distillate is about 8.5 wt. %.

As shown in Table 3, without being bound by theory, it has surprisingly and unexpectedly been discovered that when any amount of acetal is detected in the feed that is introduced to the first column 107, the acetal appears to decompose in the column such that less or even no detectable amounts are present in the distillate and/or residue.

The columns shown in FIGS. 1 and 2 may comprise any distillation column capable of performing the desired separation and/or purification. Each column preferably comprises a tray column having from 1 to 150 trays, e.g., from 10 to 100, from 20 to 95 trays or from 30 to 75 trays. The trays may be sieve trays, fixed valve trays, movable valve trays, or any other suitable design known in the art. In other embodiments, a packed column may be used. For packed columns, structured packing or random packing may be employed. The trays or packing may be arranged in one continuous column or they may be arranged in two or more columns such that the vapor from the first section enters the second section while the liquid from the second section enters the first section, etc.

The associated condensers and liquid separation vessels that may be employed with each of the distillation columns may be of any conventional design and are simplified in FIGS. 1 and 2. As shown in FIGS. 1 and 2, heat may be supplied to the base of each column or to a circulating bottom stream through a heat exchanger or reboiler. Other types of reboilers, such as internal reboilers, may also be used. The heat that is provided to the reboilers may be derived from any heat generated during the process that is integrated with the reboilers or from an external source such as another heat generating chemical process or a boiler. Although one reactor and flasher are shown, additional reactors, flashers, condensers, heating elements, and other components may be used in various embodiments of the present invention. As will be recognized by those skilled in the art, various condensers, pumps, compressors, reboilers, drums, valves, connectors, separation vessels, etc., normally employed in carrying out chemical processes may also be combined and employed in the processes of the present invention.

The temperatures and pressures employed in the columns may vary. As a practical matter, pressures from 10 kPa to 3000 kPa will generally be employed in these zones although in some embodiments subatmospheric pressures or superatmospheric pressures may be employed. Temperatures within the various zones will normally range between the boiling points of the composition removed as the distillate and the composition removed as the residue. As will be recognized by those skilled in the art, the temperature at a given location in an operating distillation column is dependent on the composition of the material at that location and the pressure of column. In addition, feed rates may vary depending on the size of the production process and, if described, may be generically referred to in terms of feed weight ratios.

Depending on the reaction conditions, the crude ethanol product exiting reactor 103 in line 112 may comprise ethanol, acetic acid (unconverted), ethyl acetate, and water. After exiting reactor 103, a non-catalyzed equilibrium reaction may occur between the components contained in the crude ethanol product until it is added to flasher 106 and/or first column 107. This equilibrium reaction tends to drive the crude ethanol product to an equilibrium between ethanol/acetic acid and ethyl acetate/water, as shown below.

$$EtOH + HOAc \leftrightarrows EtOAc + H_2O$$

In the event the crude ethanol product is temporarily stored, e.g., in a holding tank, prior to being directed to separation zone 102, extended residence times may be encountered. Generally, the longer the residence time between reaction zone 101 and separation zone 102, the greater the formation of ethyl acetate. For example, when the residence time between reaction zone 101 and separation zone 102 is greater than 5 days, significantly more ethyl acetate may form at the expense of ethanol. Thus, shorter residence times between reaction zone 101 and separation zone 102 are generally preferred in order to maximize the amount of ethanol formed. In one embodiment, a holding tank (not shown), is included between the reaction zone 101 and separation zone 102 for temporarily storing the liquid component from line 115 for up to 5 days, e.g., up to 1 day, or up to 1 hour. In a preferred embodiment no tank is included and the condensed liquids are fed directly to the first distillation column 107. In addition, the rate at which the non-catalyzed reaction occurs may increase as the temperature of the crude ethanol product, e.g., in line 115, increases. These reaction rates may be particularly problematic at temperatures exceeding 30° C., e.g., exceeding 40° C. or exceeding 50° C. Thus, in one embodiment, the temperature of liquid components in line 115 or in the optional holding tank is maintained at a temperature less than 40° C., e.g., less than 30° C. or less than 20° C. One or more cooling devices may be used to reduce the temperature of the liquid in line 115.

As discussed above, a holding tank (not shown) may be included between the reaction zone 101 and separation zone 102 for temporarily storing the liquid component from line 115, for example from 1 to 24 hours, optionally at a temperature of about 21° C., and corresponding to an ethyl acetate formation of from 0.01 wt. % to 1.0 wt. % respectively. In addition, the rate at which the non-catalyzed reaction occurs may increase as the temperature of the crude ethanol product is increased. For example, as the temperature of the crude ethanol product in line 115 increases from 4° C. to 21° C., the rate of ethyl acetate formation may increase from about 0.01 wt. % per hour to about 0.05 wt. % per hour. Thus, in one embodiment, the temperature of liquid components in line 115 or in the optional holding tank is maintained at a temperature less than 21° C., e.g., less than 4° C. or less than −10° C.

The distillate, e.g., overhead stream, of column 107 optionally is condensed and refluxed as shown in FIG. 1, preferably, at a reflux ratio of 1:5 to 10:1. The distillate in line 117 preferably comprises ethanol, ethyl acetate, and water, along with other impurities.

The first distillate in line 117 may be introduced to the light ends column, i.e., second column 108, preferably in the top part of column 108, e.g., top third. Second column 108 may be a tray column or packed column. In one embodiment, second column 108 is a tray column having from 5 to 70 trays, e.g., from 15 to 50 trays or from 20 to 45 trays. As one example, when a 25 tray column is utilized in a column without water extraction, line 117 is introduced at tray 17. Also, when a 30 tray column is used without water extraction, line 117 is introduced at tray 2.

Although the temperature and pressure of second column 108 may vary, when at about 20 kPa to 70 kPa, the temperature of the second residue exiting in line 118 from second column 108 preferably is from 30° C. to 75° C., e.g., from 35° C. to 70° C. or from 40° C. to 65° C. The temperature of the second distillate exiting in line 120 from second column 108 preferably is from 20° C. to 55° C., e.g., from 25° C. to 50° C. or from 30° C. to 45° C. Column 108 may operate at a reduced pressure, near or at vacuum conditions, to further favor separation of ethyl acetate and ethanol. In other embodiments, the pressure of second column 108 may range from 0.1 kPa to 510 kPa, e.g., from 1 kPa to 475 kPa or from 1 kPa to 375 kPa.

In one preferred embodiment, the second residue 118 comprises an ethanol product as described in Table 7 and does not require further processing. In such embodiments, the efficiency of the system 100 may be improved by reducing the need for further capital and energy to further process second residue 118 to obtain an ethanol product, having a composition as described in Table 7 below. In embodiments where the second residue 118 comprises an ethanol product, it is preferred that the second column 108 is not an extractive column.

Optionally, second column 108 may be an extractive distillation column. In such embodiments, an extraction agent, such as for example water, may be added to second column 108. If the extraction agent comprises water, it may be obtained from an external source or from an internal return/recycle line from one or more of the other columns. Optionally, the extraction agent is obtained by recycling a portion of the third residue 121' from third column 109, also referred to as the product column, and/or a portion of the effluent 159' from the weak acid recovery zone 150.

Other suitable extractive agents for second column 108 may include, for example, dimethylsulfoxide, glycerine, diethylene glycol, 1-naphthol, hydroquinone, N,N'-dimethylformamide, 1,4-butanediol; ethylene glycol-1,5-pentanediol; propylene glycol-tetraethylene glycol-polyethylene glycol; glycerine-propylene glycol-tetraethylene glycol-1,4-butanediol, ethyl ether, methyl formate, cyclohexane, N,N-dimethyl-1,3-propanediamine, N,N'-dimethylethylenediamine, diethylene triamine, hexamethylene diamine and 1,3-diaminopentane, an alkylated thiopene, dodecane, tridecane, tetradecane, chlorinated paraffins, or a combination thereof.

Exemplary components of the distillate and residue compositions for second column 108 are provided in Table 4 below. It should be understood that the distillate and residue may also contain other components, not listed, such as components derived from the feed.

TABLE 4

| SECOND COLUMN | | | |
|---|---|---|---|
| | Conc. (wt. %) | Conc. (wt. %) | Conc. (wt. %) |
| Distillate | | | |
| Ethyl Acetate | 10 to 90 | 25 to 90 | 50 to 90 |
| Acetaldehyde | 1 to 25 | 1 to 15 | 1 to 8 |
| Water | 1 to 25 | 1 to 20 | 4 to 16 |
| Ethanol | <30 | 0.001 to 15 | 0.01 to 5 |
| Acetal | <5 | 0.001 to 2 | 0.01 to 1 |

TABLE 4-continued

| SECOND COLUMN | | | |
|---|---|---|---|
| | Conc. (wt. %) | Conc. (wt. %) | Conc. (wt. %) |
| Residue | | | |
| Water | 30 to 70 | 30 to 60 | 30 to 50 |
| Ethanol | 20 to 75 | 30 to 70 | 40 to 70 |
| Ethyl Acetate | <3 | 0.001 to 2 | 0.001 to 0.5 |
| Acetic Acid | <0.5 | 0.001 to 0.3 | 0.001 to 0.2 |

The weight ratio of ethanol in the residue to distillate of the light ends column 108 preferably is at least 2:1, e.g., at least 5:1, at least 8:1, at least 10:1 or at least 15:1. The weight ratio of ethyl acetate in the residue to distillate preferably is less than 0.4:1, e.g., less than 0.2:1 or less than 0.1:1. In embodiments that use an extractive column with water as an extraction agent as the light ends column 108, the weight ratio of ethyl acetate in the residue to ethyl acetate in the distillate is less than 0.1:1.

When second column is an extractive distillation column, the residue 118 comprises ethanol and water and may be fed via line 118 to an optional third column 109, also referred to as a product column, as shown in FIGS. 1 and 2. More preferably, the residue in line 118 is introduced in the lower part of third column 109, e.g., lower half or lower third. Third column 109 recovers ethanol, which preferably is substantially pure other than the azeotropic water content, as the distillate in line 119. The distillate of third column 109 preferably is refluxed as shown, for example, at a reflux ratio of from 1:10 to 10:1, e.g., from 1:3 to 3:1 or from 1:2 to 2:1. The residue in line 121 of the third column 109, which preferably comprises primarily water, is preferably removed from the system 100 or may be partially directed to any portion of the system 100, optionally to the second column 108 via line 121'. Third column 109 is preferably a tray column as described above and preferably operates at atmospheric pressure. The temperature of the distillate exiting in line 119 from third column 109 preferably is from 60° C. to 110° C., e.g., from 70° C. to 100° C. or from 75° C. to 95° C. The temperature of the residue exiting from third column 109 preferably is from 70° C. to 115° C., e.g., from 80° C. to 110° C. or from 85° C. to 105° C. Exemplary components of the distillate and residue compositions for optional third column 109 are provided in Table 5 below. It should be understood that the distillate and residue may also contain other components, not listed, such as components derived from the feed.

TABLE 5

| THIRD COLUMN | | | |
|---|---|---|---|
| | Conc. (wt. %) | Conc. (wt. %) | Conc. (wt. %) |
| Distillate | | | |
| Ethanol | 75 to 96 | 80 to 96 | 85 to 96 |
| Water | <12 | 1 to 9 | 3 to 8 |
| Acetic Acid | <1 | 0.001 to 0.1 | 0.005 to 0.01 |
| Ethyl Acetate | <5 | 0.001 to 4 | 0.01 to 3 |
| Residue | | | |
| Water | 75 to 100 | 80 to 100 | 90 to 100 |
| Ethanol | <0.8 | 0.001 to 0.5 | 0.005 to 0.05 |
| Ethyl Acetate | <1 | 0.001 to 0.5 | 0.005 to 0.2 |
| Acetic Acid | <2 | 0.001 to 0.5 | 0.005 to 0.2 |

Any of the compounds that are carried through the distillation process from the feed or crude reaction product generally remain in the third distillate in amounts less 0.1 wt. %, based on the total weight of the third distillate composition, e.g., less than 0.05 wt. % or less than 0.02 wt. %. In one embodiment, one or more side streams may remove impurities from any of the columns 107, 108 and/or 109 in the system 100. Preferably at least one side stream is used to remove impurities from the third column 109. The impurities may be purged and/or retained within the system 100.

The distillate in line 119 may be further purified to form an anhydrous ethanol product stream, i.e., "finished anhydrous ethanol," using one or more additional separation systems, such as, for example, distillation columns (e.g., a finishing column) or molecular sieves.

Returning to second column 108, the distillate preferably is refluxed as shown, for example, at a reflux ratio of from 1:30 to 30:1, e.g., from 1:5 to 5:1 or from 1:3 to 3:1.

In one embodiment, the distillate in line 120 is fed to fourth column 123, also referred to as the acetaldehyde removal column. In fourth column 123, the distillate in line 120 fed and separated into a fourth distillate, which comprises acetaldehyde, in line 124 and a fourth residue, which comprises ethyl acetate, in line 125. The fourth distillate preferably is refluxed at a reflux ratio of from 1:20 to 20:1, e.g., from 1:15 to 15:1 or from 1:10 to 10:1, and a portion of the distillate is directly or indirectly returned to the reaction zone 101 as shown by line 124. For example, the fourth distillate of the fourth column 123 may be combined with the acetic acid feed, added to the vaporizer 110, or added directly to the reactor 103. As shown, the fourth distillate is co-fed with the acetic acid in feed line 105 to vaporizer 110. Without being bound by theory, since acetaldehyde may be hydrogenated to form ethanol, the recycling of a stream that contains acetaldehyde to the reaction zone increases the yield of ethanol and decreases byproduct and waste generation. In another embodiment (not shown), the acetaldehyde may be collected and utilized, with or without further purification, to make useful products including but not limited to n-butanol, 1,3-butanediol, and/or crotonaldehyde and derivatives.

Fourth column 123 is preferably a tray column as described above and preferably operates above atmospheric pressure. In one embodiment, the operating pressure is from 120 kPa to 5,000 kPa, e.g., from 200 kPa to 4,500 kPa, or from 500 kPa to 3,000 kPa. In a preferred embodiment, the fourth column 123 may operate at a pressure that is higher than the pressure of the other columns.

The temperature of the fourth distillate exiting in line 124 from fourth column 123 preferably is from 60° C. to 110° C., e.g., from 70° C. to 100° C. or from 75° C. to 95° C. The temperature of the fourth residue exiting from fourth column 125 preferably is from 70° C. to 115° C., e.g., from 80° C. to 110° C. or from 85° C. to 110° C. Exemplary components of the distillate and residue compositions for fourth column 123 are provided in Table 6. It should be understood that the distillate and residue may also contain other components, not listed, such as components derived from the feed.

TABLE 6

| FOURTH COLUMN | | | |
|---|---|---|---|
| | Conc. (wt. %) | Conc. (wt. %) | Conc. (wt. %) |
| Distillate | | | |
| Acetaldehyde | 2 to 80 | 2 to 50 | 5 to 40 |
| Ethyl Acetate | <90 | 30 to 80 | 40 to 75 |
| Ethanol | <30 | 0.001 to 25 | 0.01 to 20 |
| Water | <25 | 0.001 to 20 | 0.01 to 15 |

TABLE 6-continued

| FOURTH COLUMN | | | |
|---|---|---|---|
| | Conc. (wt. %) | Conc. (wt. %) | Conc. (wt. %) |
| Residue | | | |
| Ethyl Acetate | 40 to 100 | 50 to 100 | 60 to 100 |
| Ethanol | <40 | 0.001 to 30 | 0 to 15 |
| Water | <25 | 0.001 to 20 | 2 to 15 |
| Acetaldehyde | <1 | 0.001 to 0.5 | Not detectable |
| Acetal | <3 | 0.001 to 2 | 0.01 to 1 |

FIG. 3 is a schematic drawing of an embodiment of the present invention that comprises a first column 107 and second column 108 and an weak acid recovery system 150 from FIG. 2. It should be understood that in other embodiments, the separation zone 102 of FIG. 3, may be combined with the weak acid recovery system 150 in FIG. 1.

In FIG. 3, there is no third column 123, e.g., acetaldehyde column, or fourth column 109, e.g. product column. Instead the second distillate in line 120 may be purged or returned to the reaction zone 101. The second residue in line 118 comprises ethanol and water. Depending on the composition of the second residue in line 118, one or more further columns or separation units may be used to recover a final ethanol product from the second residue in line 118.

In some embodiments, removing substantially all of the water produces an anhydrous ethanol product suitable for fuel applications. Water may be removed from the second residue in line 118 using any of several different separation techniques. Particularly preferred techniques include the use of a distillation column, one or more membranes, one or more adsorption units or a combination thereof. An adsorption unit 140 may remove water (in water stream 141) from the second residue in line 118 thus producing an ethanol stream 142 comprising 97 wt. %, 99.5 wt. % or more ethanol. The adsorption unit 140 may employ a suitable adsorption agent such as zeolite 3A or 4A. In one preferred embodiment, adsorption unit 140 is a pressure swing adsorption (PSA) unit that is operated at a temperature from 30° C. to 160° C., e.g., from 80° C. to 140° C., and a pressure of from 0.01 kPa to 550 kPa, e.g., from 1 to 150 kPa. The PSA unit may comprise two to five beds. Adsorption unit 140 may remove at least 90% of the water from the second residue in line 118, and more preferably from 95% to 99.99%. Preferably at least 95% of the ethanol from the second residue in line 118 is recovered by adsorption unit 140 in ethanol stream 142, and more preferably at least 99% of the ethanol. When water stream 141 is not recycle, water stream may be purged. Water stream 141 may comprise ethanol, in which case it may be desirable to feed all or a portion of water stream 141 back to the first column 107, via optional line 143, for ethanol recovery in first distillate in line 117 and to provide an outlet for water via first residue in line 116.

Optionally, there may also be a water separator for removing a portion of the first distillate in line 117 before separation in the second column 108. Water may removed in the liquid or vapor phase. Water may be removed, for example, using an adsorption unit, membrane, molecular sieves, or a combination thereof. Suitable adsorption units include pressure swing adsorption (PSA) units and thermal swing adsorption (TSA) units. PSA unit that is operated at a temperature from 30° C. to 160° C., e.g., from 80° C. to 140° C., and a pressure of from 0.01 kPa to 550 kPa, e.g., from 1 to 150 kPa. A membrane or an array of membranes may also be employed to separate water from the first distillate in line 117.

Ethanol

The finished ethanol composition obtained by the processes of the present invention preferably comprises from 75 to 96 wt. % ethanol, e.g., from 80 to 96 wt. % or from 85 to 96 wt. % ethanol, based on the total weight of the finished ethanol composition. Exemplary finished ethanol compositional ranges are provided below in Table 7.

TABLE 7

FINISHED ETHANOL COMPOSITIONS

| Component | Conc. (wt. %) | Conc. (wt. %) | Conc. (wt. %) |
|---|---|---|---|
| Ethanol | 75 to 96 | 80 to 96 | 85 to 96 |
| Water | <12 | 1 to 9 | 3 to 8 |
| Acetic Acid | <1 | <0.1 | <0.01 |
| Ethyl Acetate | <2 | <0.5 | <0.05 |
| Acetal | <0.05 | <0.01 | <0.005 |
| Acetone | <0.05 | <0.01 | <0.005 |
| Isopropanol | <0.5 | <0.1 | <0.05 |
| n-propanol | <0.5 | <0.1 | <0.05 |

The finished ethanol composition of the present invention preferably contains very low amounts, e.g., less than 0.5 wt. %, of other alcohols, such as methanol, butanol, isobutanol, isoamyl alcohol and other $C_4$-$C_{20}$ alcohols. In one embodiment, the amount of isopropanol in the finished ethanol composition is from 80 to 1,000 wppm, e.g., from 95 to 1,000 wppm, from 100 to 700 wppm, or from 150 to 500 wppm. In one embodiment, the finished ethanol composition is substantially free of acetaldehyde, optionally comprising less than 8 wppm acetaldehyde, e.g., less than 5 wppm or less than 1 wppm.

In some embodiments, when further water separation is used, the ethanol product may be withdrawn as a stream from the water separation unit as discussed above. In such embodiments, the ethanol concentration of the ethanol product may be higher than indicated in Table 7, and preferably is greater than 97 wt. % ethanol, e.g., greater than 98 wt. % or greater than 99.5 wt. %. The ethanol product in this aspect preferably comprises less than 3 wt. % water, e.g., less than 2 wt. % or less than 0.5 wt. %.

The finished ethanol composition produced by the embodiments of the present invention may be used in a variety of applications including applications as fuels, solvents, chemical feedstocks, pharmaceutical products, cleansers, sanitizers, hydrogenation transport or consumption. In fuel applications, the finished ethanol composition may be blended with gasoline for motor vehicles such as automobiles, boats and small piston engine aircraft. In non-fuel applications, the finished ethanol composition may be used as a solvent for toiletry and cosmetic preparations, detergents, disinfectants, coatings, inks, and pharmaceuticals. The finished ethanol composition may also be used as a processing solvent in manufacturing processes for medicinal products, food preparations, dyes, photochemicals and latex processing.

The finished ethanol composition may also be used as a chemical feedstock to make other chemicals such as vinegar, ethyl acrylate, ethyl acetate, ethylene, glycol ethers, ethylamines, aldehydes, and higher alcohols, especially butanol. In the production of ethyl acetate, the finished ethanol composition may be esterified with acetic acid. In another application, the finished ethanol composition may be dehydrated to produce ethylene. Any known dehydration catalyst can be employed to dehydrate ethanol, such as those described in copending U.S. Pub. Nos. 2010/0030002 and 2010/0030001, the entire contents and disclosures of which are hereby incorporated by reference. A zeolite catalyst, for example, may be employed as the dehydration catalyst. Preferably, the zeolite has a pore diameter of at least about 0.6 nm, and preferred zeolites include dehydration catalysts selected from the group consisting of mordenites, ZSM-5, a zeolite X and a zeolite Y. Zeolite X is described, for example, in U.S. Pat. No. 2,882,244 and zeolite Y in U.S. Pat. No. 3,130,007, the entireties of which are hereby incorporated herein by reference.

In order that the invention disclosed herein may be more efficiently understood, an example is provided below. It should be understood that this example is for illustrative purposes only and is not to be construed as limiting the invention in any manner.

EXAMPLES

Several hydrogenation reactions were performed at different conversion rates as shown in Table 8. Table 8 indicates calculated concentrations examples of total ethanol (free+ esterified), water and unreacted acetic acid corresponding to hydrogenation reactor acetic acid molar conversions (%).

TABLE 8

| | | Crude Ethanol Product (Wt. %) | | |
|---|---|---|---|---|
| Example | Conversion Rate of HOAc | Ethanol | Water | Unreacted Acetic Acid |
| 1 | 40% | 29.9 | 11.7 | 58.4 |
| 2 | 50% | 37.1 | 14.5 | 48.4 |
| 3 | 60% | 44.2 | 17.3 | 38.5 |
| 4 | 70% | 51.3 | 20.1 | 28.7 |
| 5 | 80% | 58.2 | 22.8 | 19.0 |
| 6 | 90% | 65.1 | 25.5 | 9.4 |

Each of the examples were next separated in a first distillation in a similar manner as described above in FIGS. 1 and 2 with the first distillation tower overhead water composition set at 8.5 wt. %. Table 9 indicates the distillate water flow rate and the compositions of the corresponding example residue streams that that may be further processed in a weak acid recovery system.

TABLE 9

| | Distillate | | Residue | |
|---|---|---|---|---|
| Example | Water flow rate (g/min) | Water flow rate (g/min) | Water Wt. % | Unreacted Acetic Acid Wt. % |
| 1 | 2.3 | 9.9 | 15.2 | 84.8 |
| 2 | 2.9 | 12.3 | 21.7 | 78.3 |
| 3 | 3.4 | 14.7 | 30.4 | 69.6 |
| 4 | 4.1 | 17.0 | 42.5 | 57.5 |
| 5 | 4.6 | 19.3 | 60.5 | 39.5 |
| 6 | 5.2 | 21.6 | 90.3 | 9.7 |

As indicated in Table 9, the majority of water for each example is separated with the residue. Examples 1-4 are preferably processed in a weak acid recovery system of FIG. 1. Examples 5 and 6 are preferably processed in a weak acid recovery system of FIG. 2 that includes an extractor.

While the invention has been described in detail, modifications within the spirit and scope of the invention will be readily apparent to those of skill in the art. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A process for producing ethanol, comprising the steps of:
   hydrogenating acetic acid in a reactor in the presence of a catalyst to form a crude ethanol product comprising ethanol, water and unreacted acetic acid;
   separating at least a portion of the crude ethanol product in a first column into a first distillate comprising ethanol and less than 10 wt. % water, and a first residue comprising water and acetic acid;
   separating at least a portion of the first residue in an azeotrope acid-water separator column into a separated distillate comprising water, and a separated residue comprising acetic acid; and
   returning at least a portion of the separated residue to the reactor.

2. The process of claim 1, wherein the separated residue has a greater concentration of acetic acid than the first residue.

3. The process of claim 1, wherein the separated residue comprises acetic acid in an amount of greater than 97 wt. %.

4. The process of claim 1, wherein the first residue comprises acetic acid in an amount of from 5 to 100 wt. %.

5. The process of claim 1, wherein the first residue comprises water in an amount of less than 95 wt. %.

6. The process of claim 1, wherein the first distillate comprises one or more binary and/or tertiary azeotropes of water, ethanol, and/or ethyl acetate.

7. The process of claim 1, further comprising the step of:
   separating at least a portion of the first distillate in a second column into a second distillate comprising ethyl acetate and a second residue comprising ethanol.

8. The process of claim 7, wherein the second residue comprises ethanol in an amount of from 75 wt. % to 96 wt. %.

9. The process of claim 1, further comprising the step of:
   adding one or more compounds to the azeotrope acid-water separator column to form an azeotrope with water, wherein the one or more compounds is selected from the group consisting of ethyl acetate, propyl acetate, isopropyl acetate, butyl acetate, vinyl acetate, diisopropyl ether, carbon disulfide, tetrahydrofuran, isopropanol, ethanol, and $C_3$-$C_{12}$ alkanes.

10. The process of claim 1, further comprising the step of extracting at least a portion of the first residue using an azeotrope compound to yield an extract comprising at least 10 wt. % acetic acid; and introducing at least a portion of the extract to the separator column.

11. The process of claim 1, wherein the acetic acid is formed from methanol and carbon monoxide, wherein each of the methanol, the carbon monoxide, and hydrogen for the hydrogenating step is derived from syngas, and wherein the syngas is derived from a carbon source selected from the group consisting of natural gas, oil, petroleum, coal, biomass, and combinations thereof.

12. A process for producing ethanol, comprising the steps of:
   providing a crude ethanol product comprising ethanol, acetic acid, water and ethyl acetate;
   separating at least a portion of the crude ethanol product in a first column into a first distillate comprising ethanol, and a first residue comprising water and acetic acid;
   separating at least a portion of the first residue in an azeotrope acid-water separator column into a separated distillate comprising water, and a separated residue comprising acetic acid; and
   directing at least a portion of the separated residue to an ethanol synthesis reactor.

13. The process of claim 12, wherein the concentration of acetic acid in the separated residue is greater than the concentration of acetic acid in the first residue.

14. The process of claim 12, wherein the separated residue comprises acetic acid in an amount of greater than 97 wt. %.

15. The process of claim 12, wherein the first residue comprises acetic acid in an amount of from 5 to 100 wt. %.

16. The process of claim 12, wherein the first residue comprises water in an amount of less than 95 wt. %.

17. The process of claim 12, wherein the first distillate comprises one or more binary and/or tertiary azeotropes of water, ethanol, and/or ethyl acetate.

18. The process of claim 12, further comprising the step of:
   separating at least a portion of the first distillate in a second column into a second distillate comprising ethyl acetate, and a second residue comprising ethanol.

19. The process of claim 18, wherein the second residue comprises ethanol in an amount of from 75 wt. % to 96 wt. %.

20. The process of claim 12, further comprising the step of:
   adding one or more compounds to the azeotrope acid-water separator column to form an azeotrope with water, wherein the one or more compounds is selected from the group consisting of ethyl acetate, propyl acetate, isopropyl acetate, butyl acetate, vinyl acetate, diisopropyl ether, carbon disulfide, tetrahydrofuran, isopropanol, ethanol, and $C_3$-$C_{12}$ alkanes.

21. The process of claim 12, further comprising the step of extracting at least a portion of the first residue using an azeotrope compound to yield an extract comprising at least 10 wt. % acetic acid; and introducing at least a portion of the extract to the separator column.

22. A process for producing ethanol, comprising the steps of:
   hydrogenating acetic acid in a reactor in the presence of a catalyst to form a crude ethanol product;
   separating at least a portion of the crude ethanol product in a first column into a first distillate comprising ethanol, ethyl acetate, and less than 10 wt. % water, and a first residue comprising acetic acid and water; and
   separating at least a portion of the first distillate in a second column into a second distillate comprising ethyl acetate and a second residue comprising ethanol.

23. The process of claim 22, wherein the second residue comprises ethanol in an amount of from 75 wt. % to 96 wt. %.

24. A process for producing ethanol, comprising the steps of:
   hydrogenating acetic acid in a reactor in the presence of a catalyst to a conversion of at least 90% to form a crude ethanol product comprising ethanol, water and unreacted acetic acid;
   separating at least a portion of the crude ethanol product in a first column into a first distillate comprising ethanol, and a first residue comprising water and acetic acid;
   separating at least a portion of the first residue in a separator column into a separated distillate comprising water, and a separated residue comprising acetic acid; and
   returning at least a portion of the separated residue to the reactor.

25. A process for producing ethanol, comprising the steps of:
hydrogenating acetic acid in a reactor in the presence of a catalyst to a conversion of at least 90% to form a crude ethanol product;
separating at least a portion of the crude ethanol product in a first column into a first distillate comprising ethanol, ethyl acetate, and less than 10 wt. % water, and a first residue comprising acetic acid and water; and
separating at least a portion of the first distillate in a second column into a second distillate comprising ethyl acetate and a second residue comprising ethanol.

\* \* \* \* \*